United States Patent [19]

Siskin et al.

[11] Patent Number: 5,043,486

[45] Date of Patent: Aug. 27, 1991

[54] AQUATHERMOLYTIC CLEAVAGE OF ETHERS

[75] Inventors: Michael Siskin, Livingston; Glen B. Brons, Phillipsburg; Ramzi Y. Saleh, Flemington; Stephen N. Vaughn, Annandale, all of N.J.

[73] Assignee: Exxon Research and Engineering Company, Florham Park, N.J.

[21] Appl. No.: 572,485

[22] Filed: Aug. 23, 1990

[51] Int. Cl.$^5$ .................... C07C 29/10; C07C 31/10; C07C 31/12; C07C 31/135

[52] U.S. Cl. .................................. 568/907; 568/835; 585/639

[58] Field of Search ............................... 568/907, 835

[56] References Cited

U.S. PATENT DOCUMENTS

| | | | |
|---|---|---|---|
| 2,045,785 | 6/1936 | Lewis | 260/156 |
| 2,519,061 | 8/1950 | Mason | 260/632 |
| 2,776,318 | 1/1957 | Willke et al. | 568/907 |
| 4,357,147 | 11/1982 | Bezman | 44/56 |
| 4,368,337 | 1/1983 | Tawara et al. | 568/907 |
| 4,395,580 | 7/1983 | Juguin et al. | 585/639 |
| 4,405,822 | 9/1983 | Bezman | 568/899 |
| 4,551,560 | 11/1985 | Rizkalla | 568/907 |
| 4,581,475 | 4/1986 | Neier et al. | 568/907 |
| 4,751,343 | 6/1988 | Reinhardt et al. | 585/639 |
| 4,804,704 | 2/1989 | Schleppinghoff et al. | 524/549 |

FOREIGN PATENT DOCUMENTS

| | | | |
|---|---|---|---|
| 137433 | 4/1985 | European Pat. Off. | 568/907 |
| 0302336 | 2/1989 | European Pat. Off. | |
| 162829 | 11/1964 | U.S.S.R. | 568/907 |

Primary Examiner—J. E. Evans

[57] ABSTRACT

The present invention provides for a simplified process for converting ethers into their corresponding alcohols comprising forming an aqueous mixture of the ether and at least about 50% by weight water and heating the mixture under autogeneous pressure at a temperature of from about 250° to 450° C., more preferably from about 250° C. up to the critical temperature of water which is about 374° C. Heating is continued for a period of time sufficient to convert at least about 20% by weight of the ether, usually from about 5 up to about 120 minutes, depending on temperature and the amount of water present, and the identity of the starting ether feedstock.

The process may be characterized as an aquathermolysis reaction wherein the reaction proceeds in water primarily through ionic routes rather than through free radical routes. Accordingly, relatively high conversion rates and good yields of alcohol and other reaction by-products may be obtained without the necessity of using a catalyst in the process.

25 Claims, No Drawings

AQUATHERMOLYTIC CLEAVAGE OF ETHERS

This application is related to copending application Ser. No. 07/411,121, filed Sept. 22, 1989.

BACKGROUND OF THE INVENTION

1. Field of the Invention

The present invention relates to a process for converting ethers to alcohols, and particularly to a process for the aquathermolysis of ethers in an aqueous environment.

2. Description of Related Art

Various processes are described in the prior art for the conversion of ethers into a mixture comprising predominantly alcohols and olefins.

Generally speaking, ethers are less commercially valuable than the corresponding alcohol and olefin reaction products which may be produced by cleavage of the ether. This is particularly important from the economic standpoint when such ethers are formed as an undesirable by-product in chemical reactions. For example, aliphatic alcohols are commercially manufactured by hydrating the appropriate monoolefin in the presence of an acid catalyst. The reaction product usually contains minor quantities of the corresponding alkyl ether as a low-value by-product. More specifically, the hydration of propylene with sulfuric acid generally yields a reaction mixture comprising isopropyl alcohol and up to about 20% by weight of isopropyl ether as a by-product. Also, during the commercial manufacture of methyl ethyl ketone by the hydration of n-butene to sec-butyl alcohol, followed by oxidation of the alcohol over a fixed bed catalyst, substantial quantities of sec-butyl ether are generated which is also a low-value product.

Prior art processes for the conversion of ethers into alcohols generally involve cleavage of the ether in an aqueous or non-aqueous medium and in the presence of an acidic catalyst.

For example, U.S. Pat. No. 2,045,785 discloses the conversion of ethers such as ethyl ether to alcohols such as ethanol by a process wherein the ether is converted using a dilute aqueous solution of an acid catalyst by subjecting the mixture to temperatures within the range of 200° to 300° C. and pressures of from about 225 to 3000 psig. for a period of from about 10 to 60 minutes. Preferred acids are stronger acids such as sulfuric, phosphoric or hydrochloric, but weaker acids such as acetic are also disclosed, and the acid concentration in the aqueous medium ranges from 5 to 20%. Salts which are acidic in aqueous medium may also be employed as catalysts.

It is to be noted in Examples 1–3 that where HCl is the catalyst, the amount of ethylene obtained in addition to ethanol is a function of the time of the reaction and the temperature of the reaction.

U.S. Pat. No. 2,519,061 discloses a process for cleaving ethers to form alcohols by passing an aqueous mixture of the ether over a catalyst comprising metal oxides at temperatures within the range of 350° to 800° F. and pressures from atmospheric up to 200 atmospheres.

U.S. Pat. No. 4,357,147 discloses a process for producing an oxygenated fuel blending stock by hydration and oligomerization of propylene, wherein the isopropyl ether by-product is converted to propylene, isopropyl alcohol, and water in a reversion zone using alumina or a zeolite as the catalyst. U.S. Pat. No. 4,405,822 teaches a related process for producing alcohols by olefin hydration, wherein the ether by-product is converted using a large molar excess of water in the presence of an acid ion exchange resin.

U.S. Pat. No. 4,751,343 teaches the preparation of tertiary olefins with simultaneous production of alcohols by cleavage of tertiary alkyl ethers when mixed with water over strong acid cation exchangers. U.S. Pat. No. 4,804,704 describes cross-linked acidic resins suitable for use in cleaving tertiary ethers. EP-302,336 teaches tertiary ether cleavage using a column apparatus containing an acidic ion exchange resin and employing a stream of deionized water.

U.S. Pat. No. 4,395,580 teaches the production of tertiary olefins by decomposing tertiary ethers with steam over an alumina catalyst containing Ti, Zr and/or Hf.

U.S. Pat. No. 4,581,475 teaches the direct conversion of aliphatic ethers to aliphatic alcohols by reacting the ether with an excess of water at high temperature and at a pressure sufficient to keep the reactants in the liquid phase and in the presence of a strong acid ion exchanger.

While these and similar processes are generally effective and efficient insofar as they go, they all suffer from the requirement that catalysts are used in the processes. In commercial processes, the presence of significant levels of acidic catalyst materials in the production of liquids and gases gives rise to corrosive problems with respect to production equipment and additional production expense with respect to the disposition of acidic effluents in an environmentally acceptable manner. The utilization of "bed" catalysts such as zeolites or acidified polymeric materials requires frequent catalyst regeneration or replacement which diminishes the economy of the process.

SUMMARY OF THE INVENTION

The present invention provides for a simplified process for converting ethers into their corresponding alcohols comprising forming an aqueous mixture of the ether and at least about 50% by weight water and heating the mixture under autogeneous pressure at a temperature of from about 250° to 450° C., more preferably from about 250° C. up to the critical temperature of water which is about 374° C. Heating is continued for a period of time sufficient to convert at least about 20% by weight of the ether, usually from about 5 up to about 120 minutes, depending on temperature, the amount of water present and the identity of the starting ether feedstock.

The process may be characterized as an aquathermolysis reaction wherein the reaction proceeds in water primarily through ionic routes rather than through free radical routes. Accordingly, relatively high conversion rates and good yields of alcohol and other reaction by-products may be obtained without the necessity of using a catalyst in the process.

DETAILED DESCRIPTION OF THE INVENTION

As indicated above, the present invention is based on the discovery that a C—O bond in ethers may be cleaved in an aqueous medium. The ionic reaction mechanism is facilitated largely as a consequence of the favorable changes that occur in the chemical and physical properties of water at temperatures between about 250° C. up to the critical temperature which is about 374° C. These changes are manifest by water which has a higher dissociation constant, a lower density and a lower dielectric constant. These properties generally increase the solubility of ethers in water and help facilitate ionic reaction pathways in aqueous systems.

The invention is applicable to the cleavage of one or a mixture of different ethers having the general formula 1:

$$R(OR')_n \qquad (1)$$

wherein n is a whole number ranging from 1 to 4, R and R' may be the same or different and are selected from the group consisting of linear or branched aliphatic groups containing from 1 to about 30 carbon atoms and cycloaliphatic groups containing from 3 to about 25 carbon atoms.

Inclusive of such ethers are diethers and triethers where n in formula 1 is greater than such as ethylene glycol dimethyl ether. More preferred diethers include $C_1$ to $C_{10}$ diethers such as trimethyl diether, triethyl diether and so on up to about tridecyl diether.

Also included within the scope of formula 1 are simple monoethers wherein n is 1. Such ethers include branched or linear aliphatic ethers such as methyl ether, methyl ethyl ether, ethyl ether, n-propyl ether, isopropyl ether, sec-butyl -ether, methyl n-butyl ether, ethyl n-butyl ether, n-butyl ether, n-amyl ether, isoamyl ether, n-hexyl ether, n-decyl ether and the like. The more preferred monoethers are those wherein R and R, above contain from 1 to about 15 carbon atoms.

The process is also applicable to ethers containing one or more cycloaliphatic groups such as cyclohexyl alkyl ethers, including cyclohexyl ether, cyclohexyl ethyl ether, cyclohexyl butyl ether and the like.

The terms aliphatic and cycloaliphatic as used herein are also intended to be inclusive of such groups containing one or more non-interfering substituent groups replacing hydrogen on the carbon chain.

Although ordinary tap water may be used in the process, it is preferred to use distilled or deionized water substantially free of dissolved salts and particularly preferred to use water which has been deoxygenated and is substantially free of dissolved oxygen. Removal of oxygen tends to minimize the occurrence of free radical side reactions during the process.

The amount of water used in forming the mixture with the ether may generally range from at least about 50% by weight up to about 97% by weight, i.e., the mixture may contain from about 1 to 30 parts by weight water per part by weight of ether. In general, the higher the water content of the mixture within the above specified range, the greater the conversion of the ether at any given process temperature within the 250° to 450° C. range.

Conversely, the higher the process temperature within that range, the less water is required to give rise to higher conversion rates of the ether. The preferred water content of the mixture ranges from about 2 to about 15 parts by weight per part by weight of ether, with 2 to 10 parts by weight being most preferred.

As indicated above, the process is conducted by introducing the water and ether into a reaction vessel and heating the mixture under autogeneous pressure and preferably in an inert atmosphere, such as argon or nitrogen, as an aid in excluding oxygen from the system, and at a temperature within the range of from about 250° to 450° C. for a period of time such that at least about 20% by weight of the ether is cleaved or converted into other products. Normally, the process is conducted at a temperature not higher than the critical temperature of water which is about 374° C., but supercritical temperatures above that and up to about 450° C. may also be utilized. Good results in terms of the percentage of ether converted and yield of alcohol realized are achieved with process temperatures within the range of from about 300° to 374° C.

Acceptable ether conversion rates of at least about 20% by weight may be achieved by conducting the reaction over a time period of as little as 5 minutes up to 120 minutes or more. At higher temperatures and/or with higher water/ether ratios, less time is required to achieve good ether conversion rates and vice versa. Most preferably the water content and reaction temperatures are such as to achieve ether conversion rates of at least about 30% by weight within 10 to 60 minutes, more preferably within 10 to 30 minutes.

The term "autogeneous pressure of the system" refers to the combined vapor pressure exerted by the mixed components present in the aqueous system heated at a particular process temperature. The autogeneous pressure of water alone in such a system ranges from about 500 to about 3200 psia over a temperature range of from about 250° C. up to about 374° C. Obviously, the autogeneous pressure of a system containing both water and the ether would be higher over this temperature range as a function of the ether content and the partial pressure exerted by the ether.

Since it is believed that the reaction process of this invention proceeds largely via an ionic reaction mechanism in the aqueous medium, it is not necessary and indeed undesirable from the environmental standpoint to include catalyst components in the reactant mixture. Thus, in the preferred embodiment, the reaction mixture "consists of" a mixture of water and ether. However, in some cases it may be desirable to add small quantities of a stronger or weaker acid to the reaction mixture, since it has been found that the presence of the acid enhances the ionic reaction mechanism and generally gives rise to higher rates of conversion of the ether starting material.

Thus, in a second embodiment of the invention, the reaction mixture may "consist essentially of" a mixture of water and ether, and may further include less than 3% by weight of stronger or weaker acid component sufficient to develop a weakly acidic aqueous mixture having a pH within the range of from about 3.5 up to about less than 7 at room temperature. The addition of stronger acids such as sulfuric, hydrochloric or phosphoric to the aqueous reaction media at levels of less than about 0.5% by weight gives rise to higher ether conversion rates but tends to disfavor selectivity towards the yield of alcohols and favor selectivity towards the production of olefins or other by-products. In partial contrast, the addition of weaker acids such as acetic acid or finely divided aluminosilicate materials to the aqueous reaction medium at levels of less than about 3% by weight also tends to give rise to higher ether conversion rates, but greater selectivity towards the yield of alcohols. Thus, the process may be further modified by the inclusion of acidic materials in the reaction media to enhance ether conversion and influence selectivity towards the production of alcohols on the one hand or other by-products on the other hand, depending on the identity of, strength of and concentration of the acid.

The reaction mixture may also include small quantities of an ionic surfactant stable at higher temperatures to assist in enhancing the dispersibility of the ether in the water, particularly where higher molecular weight ethers are present.

The term "conversion" as used herein is defined as C—O bond cleavages in ethers to produce more desirable value added chemical compounds. Where the starting ethers are aliphatic or cycloaliphatic ethers, the product of the reaction generally comprises a mixture composed primarily of the corresponding alcohol and olefin. For example, cleavage of an alkyl ether such as ethyl ether gives rise to predominantly ethanol and ethylene as a mixed reaction product; cleavage of isopropyl ether gives rise to predominantly isopropyl alcohol and propylene as a mixed reaction product; cleavage of sec-butyl ether gives rise to a mixture of predominantly sec-butyl alcohol and n-butane; cleavage of cyclohexyl ethyl ether gives rise to a mixture of predominantly ethanol and 1-methylcyclopentene; and so forth.

The percentage of conversion of starting ethers which may be achieved in accordance with the process of this invention may generally range from at least about 20% up to 100%, depending upon reaction conditions, and the selectivity of the process toward the production of alcohols may generally range from about 20% up to about 65% or more, once again depending on reaction conditions. The process may be tailored within the process parameters described herein to balance maximum conversion of the starting ether with favorable selectivity towards the desired reaction product, whether it be alcohol, olefin or other achievable reaction products.

The process of the present invention may be particularly adapted for use in conjunction with other chemical processes wherein ethers are formed as a less valuable by-product, including processes as are generally described in the patents recited in the Background section of the disclosure. For example, alcohols may be prepared commercially by the hydration of olefins with a strong acid such as sulfuric acid, and the reaction product invariably contains some quantity of an aliphatic or cycloaliphatic ether derived from the olefin chain mixed with the alcohol. These ethers may be readily separated from the alcohol mixture by distillation of other conventional separation techniques, and subjected to the present process to produce additional alcohol and olefin. The olefin may then be readily separated from the reaction mixture and recycled to the main process for further production of alcohol, or may be removed for other uses. The advantageous use of the present process in conjunction with other chemical processes where ethers are formed as by-products should be evident to the skilled practitioner.

The process of this invention may be carried out batchwise or in the continuous mode using conventional pressure equipment. Examples of such equipment includes a laboratory bomb, a high pressure autoclave, a stirred tank reactor or a continuous flow-through tube, each equipped with a heating means capable for achieving and maintaining the required temperatures and pressures over the required time period.

The following examples are illustrative of the invention.

EXAMPLE 1

Reagent grade isopropyl ether (1.06 g) was added to deoxygenated distilled water (6.0 g) in a 316 stainless steel reactor bomb having a capacity of 11 cc. The reactor was sealed under argon and the reaction mixture was heated in a sand bath for 15 minutes at 315° C. The reactor was then cooled to room temperature. The reaction mixture was extracted with diethyl ether.

Analysis of the extract by Gas Chromatography (FID) showed a 97 to 99% conversion of the isopropyl ether to a mixture of isopropyl alcohol and propylene, each present at an approximate 1:1 ratio. Small amounts of benzene (<0.1%) were also formed.

EXAMPLE 2

Reagent grade sec-butyl ether (1.0 g) was added to deoxygenated distilled water (5.0 g) and the process of Example 1 was repeated except that the reaction time was 30 minutes.

GC analysis of the reaction product showed a 60% conversion of the ether to sec-butyl alcohol (46% by weight) and n-butene (54% by weight).

EXAMPLE 3

The process of Example 1 was repeated except that the reaction was conducted at 250° C. for 60 minutes.

GC analysis of the reaction product showed a 35% conversion of the ether to isopropyl alcohol (35% by weight) and propylene (65% by weight).

EXAMPLE 4

Example 2 was repeated except that the reaction was conducted at 250° C. for 60 minutes.

GC analysis of the reaction product showed a 22% conversion of the ether to sec-butyl alcohol (32% by weight) and n-butene (68% by weight).

EXAMPLE 5

Example 1 was repeated except that 0.1% by weight of concentrated sulfuric acid was included in the aqueous reactant mixture and the reaction was conducted for 10 minutes instead of 15 minutes.

GC analysis of the reaction product showed 100% conversion of the ether to isopropyl alcohol (29% by weight) and propylene (71% by weight).

EXAMPLE 6

Example 1 was repeated except that 2% by weight of acetic acid was included in the aqueous reactant mixture and the reaction was conducted for 10 minutes instead of 15 minutes.

GC analysis of the reaction product showed 95% conversion of the ether to isopropyl alcohol (55% by weight) and propylene (45% by weight).

A comparison of the results achieved in Example 3 and 4 as compared with Examples 1 and 2 establishes the fact that higher conversion rates and shorter reaction times are achieved at higher temperatures. The data also illustrate that lower reaction temperatures tend to favor selectivity towards olefin production. A comparison of the results achieved in Examples 5 and 6 with those of Examples 1 and 2 illustrates that the inclusion of minor quantities of an acid in the reaction medium gives rise to high conversion rates during a shorter reaction time period, with the strong acid tending to favor olefin selectivity and the weaker acid tending to favor alcohol selectivity.

EXAMPLES 7-26

A number of additional experiments were conducted in accordance with the process of Example 1 except that the reaction times, reaction temperatures and weight ratio of water to ether reactant were varied as shown in Table 1. The abbreviations in the Table are as follows: IPE is isopropyl ether; IPA is isopropyl alcohol; SBE is sec-butyl ether; and SBA is sec-butyl alcohol. The % conversion of the starting ether and the selectivity and yield (% conversion multiplied by selectivity) of alcohol produced under the various process parameters are as shown in the Table.

TABLE 1

| EXAMPLE | ETHER | TIME/MIN | TEMP °C. | H₂O/ETHER RATIO | WT. % CONVERSION | WT. % ALCOHOL SELECTIVITY | WT. % ALCOHOL YIELD |
|---|---|---|---|---|---|---|---|
| 7  | IPE | 20 | 315 | 2  | 33  | 51 IPA | 17 |
| 8  | IPE | 30 | 315 | 2  | 38  | 60 IPA | 23 |
| 9  | IPE | 10 | 315 | 5  | 52  | 48 IPA | 25 |
| 10 | IPE | 20 | 315 | 5  | 61  | 61 IPA | 37 |
| 11 | IPE | 30 | 315 | 5  | 92  | 62 IPA | 57 |
| 12 | IPE | 10 | 315 | 10 | 77  | 50 IPA | 39 |
| 13 | IPE | 20 | 315 | 10 | 90  | 60 IPA | 54 |
| 14 | IPE | 10 | 360 | 2  | 25  | 24 IPA | 6  |
| 15 | IPE | 20 | 360 | 2  | 28  | 25 IPA | 7  |
| 16 | IPE | 30 | 360 | 2  | 32  | 36 IPA | 12 |
| 17 | IPE | 10 | 360 | 5  | 84  | 56 IPA | 47 |
| 18 | IPE | 20 | 360 | 5  | 99  | 50 IPA | 50 |
| 19 | IPE | 30 | 360 | 5  | 100 | 57 IPA | 57 |
| 20 | IPE | 10 | 360 | 10 | 88  | 61 IPA | 54 |
| 21 | IPE | 20 | 360 | 10 | 99  | 55 IPA | 55 |
| 22 | IPE | 30 | 360 | 10 | 99  | 36 IPA | 36 |
| 23 | SBE | 30 | 315 | 2  | 33  | 35 SBA | 12 |
| 24 | SBE | 30 | 315 | 5  | 63  | 43 SBA | 27 |
| 25 | SBE | 60 | 315 | 5  | 84  | 41 SBA | 34 |
| 26 | SBE | 20 | 360 | 5  | 98  | 38 SBA | 37 |

What is claimed is:

1. A process for converting ethers into their corresponding alcohols comprising forming an aqueous mixture consisting essentially of said ether and at least about 50% by weight water, heating said mixture at a temperature within the range of from about 250° up to about 450° C. under the autogeneous pressure of the system and for a period of time sufficient to convert at least about 20% by weight of said ether, and recovering said alcohol.

2. The process of claim 1 wherein said ether is one or a mixture of different ethers having the structure:

R(OR')$_n$ wherein n is a whole number ranging from 1 to 4, R and R' may be the same or different and are selected from the group consisting of linear or branched aliphatic groups containing from 1 to about 30 carbon atoms and cycloaliphatic groups containing from 3 to about 25 carbon atoms.

3. The process of claim 2 wherein n is 1 and R and R' are selected from the group consisting of linear or branched aliphatic groups containing from 1 to about 30 carbon atoms.

4. The process of claim 3 wherein said aqueous mixture contains up to about 30 parts by weight water per part by weight of ether.

5. The process of claim 4 wherein said aqueous mixture contains from about 2 to about 15 parts by weight water per part by weight ether.

6. The process of claim 3 wherein said mixture is heated at a temperature of up to about 374° C.

7. The process of claim 6 wherein said mixture is heated at a temperature of from about 300° up to about 374° C.

8. The process of claim 6 wherein said aqueous mixture is heated for a period of time of from about 5 to about 120 minutes.

9. The process of claim 8 wherein said aqueous mixture is heated for a period of time of from about 10 to about 60 minutes.

10. The process of claim 6 wherein said ether is isopropyl ether.

11. The process of claim 6 wherein said ether is sec-butyl ether.

12. The process of claim 1 wherein said aqueous mixture contains less than about 3% by weight of an organic or inorganic acid sufficient to develop a weakly acidic aqueous mixture having a pH within the range of from about 3.5 up to about less than 7 at room temperature.

13. The process of claim 12 wherein said acid is selected from the group consisting of sulfuric, hydrochloric and phosphoric acids and is present in said aqueous mixture at a level of less than about 0.5% by weight.

14. The process of claim 12 wherein said acid is acetic acid.

15. The process of claim 6 wherein said water is deoxygenated water.

16. A process for converting ethers into their corresponding alcohols comprising forming an aqueous mixture consisting of said ether and at least about 50% by weight water and heating said mixture at a temperature within the range of from about 250° C. up to the critical temperature of water under the autogeneous pressure of the system and for a period of time ranging from about 5 to about 120 minutes, and recovering said alcohol.

17. The process of claim 16 wherein said ether is one or a mixture of different ethers having the structure:

R(OR')$_n$ wherein n is a whole number ranging from 1 to 4, R and R' may be the same or different and are selected from the group consisting of linear or branched aliphatic groups containing from 1 to about 30 carbon atoms and cycloaliphatic groups containing from 3 to about 25 carbon atoms.

18. The process of claim 17 wherein n is 1 and R and R' are selected from the group consisting of linear or branched aliphatic groups containing from 1 to about 30 carbon atoms.

19. The process of claim 18 wherein said aqueous mixture contains up to about 30 parts by weight water per part by weight of ether.

20. The process of claim 19 wherein said aqueous mixture contains from about 2 to about 15 parts by weight water per part by weight ether.

21. The process of claim 20 wherein said mixture is heated at a temperature of from about 300° up to about 374° C.

22. The process of claim 21 wherein said aqueous mixture is heated for a period of time of from about 10 to about 60 minutes.

23. The process of claim 22 wherein said ether is isopropyl ether.

24. The process of claim 22 wherein said ether is sec-butyl ether.

25. The process of claim 21 wherein said water is deoxygenated water.

* * * * *